(12) United States Patent
Burbank

(10) Patent No.: US 8,771,270 B2
(45) Date of Patent: Jul. 8, 2014

(54) BIPOLAR CAUTERY INSTRUMENT

(75) Inventor: William A. Burbank, Sandy Hook, CT (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 1272 days.

(21) Appl. No.: 12/173,913

(22) Filed: Jul. 16, 2008

(65) Prior Publication Data

US 2010/0016853 A1  Jan. 21, 2010

(51) Int. Cl.
*A61B 18/14* (2006.01)

(52) U.S. Cl.
USPC ............................................. 606/51

(58) Field of Classification Search
USPC .......... 606/32, 50–52, 206–209; 607/98, 100, 607/115
See application file for complete search history.

(56) References Cited

U.S. PATENT DOCUMENTS

| | | |
|---|---|---|
| 5,295,990 A | 3/1994 | Levin |
| 5,396,900 A | 3/1995 | Slater et al. |
| 5,833,656 A | 11/1998 | Smith et al. |
| 6,331,181 B1 | 12/2001 | Tierney et al. |
| 6,491,691 B1 | 12/2002 | Morley et al. |
| 6,840,938 B1 | 1/2005 | Morley et al. |
| 7,422,592 B2 | 9/2008 | Morley et al. |
| 8,012,154 B2 * | 9/2011 | Livneh .............................. 606/52 |
| 2004/0162557 A1 * | 8/2004 | Tetzlaff et al. .................... 606/51 |
| 2006/0190034 A1 * | 8/2006 | Nishizawa et al. ........... 606/205 |
| 2007/0123855 A1 * | 5/2007 | Morley et al. .................... 606/48 |
| 2008/0046122 A1 | 2/2008 | Manzo et al. |

FOREIGN PATENT DOCUMENTS

| | | |
|---|---|---|
| EP | 624348 A2 | 11/1994 |
| WO | WO2008045350 | 4/2008 |

OTHER PUBLICATIONS

Vertut, Jean et al., *Robot Technology: Teleoperation and Robotics Evolution and Development*, 1986, vol. 3A, 332 pages, English translation Prentice-Hall, Inc., Inglewood Cliffs, NJ, USA.
PCT/US09/50681 International Search Report and Written Opinion of the International Searching Authority, mailed Jan. 22, 2010, 17 pages.
PCT/US09/50681 Second Written Opinion of the International Searching Authority, mailed Aug. 6, 2010, 7 pages.
PCT/US09/50681 Partial International Search Report and Invitation to Pay Additional Fees, mailed Sep. 24, 2009, 5 pages.

* cited by examiner

*Primary Examiner* — Michael Peffley
*Assistant Examiner* — Thomas Giuliani

(57) ABSTRACT

A cautery instrument includes a brush-type contact providing a sliding electrical connection to a jaw of the instrument. To provide isolation, the jaws may have ends in cavities in a clevis made of an insulating material. Non-conducting drive cables can be attached to the jaws using high friction paths that prevent or resist slippage of the cables relative to the jaws.

22 Claims, 7 Drawing Sheets

BIPOLAR CAUTERY INSTRUMENT

CROSS-REFERENCE TO RELATED APPLICATIONS

This patent document is related to and incorporates by reference co-filed U.S. patent application Ser. No. 12/173,934, entitled, "Four-Cable Wrist with Solid Surface Cable Channels," and co-filed U.S. patent application Ser. No. 12/173,928, entitled, "Backend Mechanism for Four-Cable Wrist".

BACKGROUND

Robotically controlled surgical instruments are often used in minimally invasive medical procedures. One architecture for such instruments includes an effector or tool such as forceps, a cutting tool, or a cauterizing tool mounted on a wrist mechanism at the distal end of an extension, sometimes referred to herein as the main tube of the instrument. During a medical procedure, the effector and the distal end of the main tube can be inserted into a small incision or a natural orifice of a patient to position the effector at a work site within the body of the patient. The wrist mechanism can then be used to move and operate the effector when performing the desired procedure at the work site. Cables or similar structures extending through the main tube of the instrument can connect the wrist mechanism to a transmission sometimes referred to herein as a backend mechanism. For robotic control of the effector and wrist mechanism, the backend mechanism is motor driven, and a processing system may be used to provide a user interface for a doctor to control the instrument.

The wrist mechanism generally provides specific degrees of freedom for movement of the effector. For example, for forceps or other grasping tools, the wrist may be able to change the pitch, yaw, and grip of the effector. More degrees of freedom could be implemented through the wrist, but implementing three degrees of freedom in the wrist and implementing other degrees of freedom such as roll or insertion/extraction through movement of the main tube generally provides the motions necessary for performing medical procedures.

A conventional architecture for a wrist mechanism in a robotically controlled medical instrument uses cables to turn a capstan in the wrist mechanism and thereby rotate the portion of the wrist mechanism that is connected to the capstan. For example, a wrist mechanism can include three capstans for rotations about a pitch axis, a yaw axis, or a grip axis. Each capstan can be controlled using two cables that are attached to the capstan so that one side pays out cable while the other side pulls in an equal length of cable. With this architecture, three degrees of freedom call for a total of six cables extending from the wrist mechanism back along the length of the main tube to the backend mechanism of the instrument. Efficient implementation of a wrist mechanism can be complicated because the cables must be carefully routed through the wrist mechanism to maintain cable tension throughout the range of motion of the wrist mechanism and to minimize the interactions (or coupling effects) of one rotation axis upon another. Further, pulleys are generally needed to reduce cable friction, which extends instrument life and permits operation without excessive forces being applied to the cables or other structures in the wrist mechanism. Cauterizing tools present a further complication for an instrument with a wrist because cauterizing instruments require delivery of electrical power to a movable effector. For example, a bipolar cauterizing tool requires delivery of opposite polarity voltages, room for movement of conductors, and effective isolation of electrical voltages.

A wrist mechanism is desired that can be operated with a small number of cables to facilitate miniaturization of the instrument and reduce costs of the instrument. A low part count for the wrist mechanism is desired to reduce manufacturing cost. Further, the wrist mechanism should allow electrical isolation suitable for a cauterizing instrument and have an efficient backend mechanism.

SUMMARY

In accordance with an aspect of the invention, an instrument suitable for minimally invasive medical procedures has a wrist mechanism that can control the pitch, yaw, and grip of an effector using only four cables that extend from the wrist through the main tube of the instrument to a backend mechanism. In accordance with a further aspect of the invention, the backend mechanism connects the four cables to three motor driven mechanisms that collectively control the pitch, yaw, and grip of the effector. In one embodiment, the effector is a bipolar cauterizing tool that employs a brush type or sliding contact for electrical connection to a movable part of the effector.

One specific embodiment of the invention is a cauterizing instrument that includes a jaw, a conductor, and a contact. The jaw is rotatably mounted, and the contact, which is on the electrical conductor, makes electrical contact to a surface of the jaw and slides on that surface when the jaw rotates. Rotation of the jaw can be controlled using non-conductive cables that follow a high friction path through the jaw.

Another embodiment of the invention is a medical instrument including a backend mechanism that may be fitted to a robotic control system. A main tube extends from the backend mechanism, and a clevis that is made of an insulating material is rotatably mounted at a distal end of the main tube. Jaws are connected to rotate about a pin of the clevis. To provide electrical power to the jaws, a first contact at the end of a conductor that extends through the main tube make electrical contact to a surface of one of the jaws and slides on the surface when the jaw rotates.

Yet another embodiment of the invention is a method for electrically energizing an effector in a medical instrument. The method includes pressing a contact against a surface of a conductive component of the effector and moving the component during a medical procedure. Moving the component causes the first contact to slide on the first surface. However, the method can still apply an electrical signal to the component through the contact.

BRIEF DESCRIPTION OF THE DRAWINGS

Use of the same reference symbols in different figures indicates similar or identical items.

DETAILED DESCRIPTION

Figure 1:
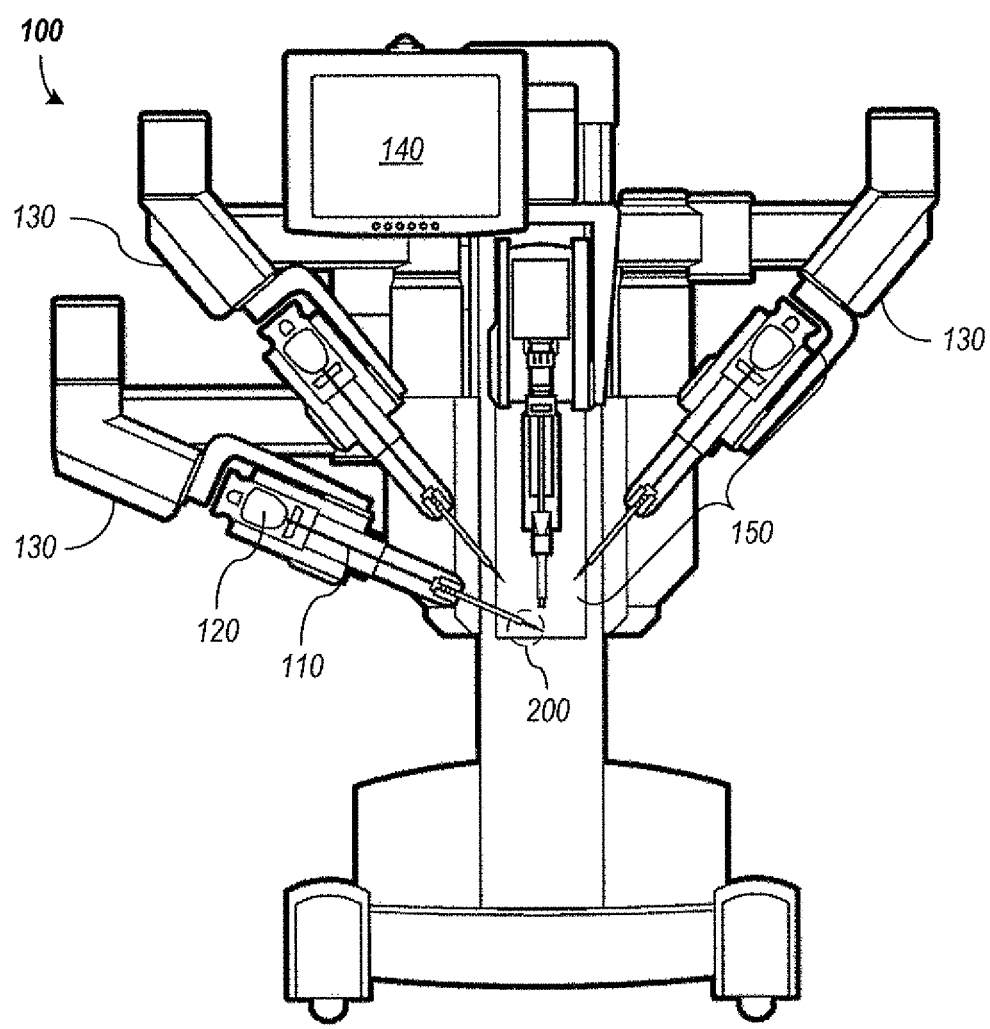
FIG. 1 shows a robotically controlled system employing a medical instrument in accordance with an embodiment of the invention.

In accordance with an aspect of the invention, a wrist mechanism for a medical instrument provides three degrees of freedom (pitch, yaw, and grip) for an effector or tool and uses only four drive cables. The wrist architecture includes a proximal clevis defining a pivot axis for pitch control and a distal clevis defining a pivot axis for yaw and grip control. The drive cables slide on the surfaces of guide channels that are integrated into the clevises so that neither pulleys nor large cable wrap angles are required. In particular, the devises can include integral cable-guiding surfaces that cradle opposing sides of a cable, and the cable guiding surfaces can be curved in multiple directions to eliminate the need for large cable wrap angles that some prior wrist architectures require. The cable-guiding surfaces are additionally constructed or curved to avoid derailment of the cables and to keep the cables within the diameter constraint of a cannula through which the wrist mechanism may be inserted or removed during a minimally invasive medical procedure. The wrist mechanism can provide the advantages of: requiring few cables and eliminating the space requirements of pulleys thereby allowing a clinically beneficial smaller working volume for the wrist mechanism; eliminating the cost of additional parts such as pulleys; and reducing friction when compared to wrist architectures with greater cable wrap angles.

In accordance with another aspect of the invention, portions of the cables that pull jaws of the instrument together for gripping can be stiffer, e.g., have a larger diameter, than the other cables in the instrument. For example, in a four-cable wrist architecture, two out of the four cables can have portions that are larger than corresponding portions of the other cables. The larger diameters of the selected cables permit use of greater gripping force, without scaling up the size of the entire instrument.

In accordance with another aspect of the invention, a wristed cauterizing instrument can use a brush or similar sliding contact to make electrical connections to jaws of the instrument. To provide electrical isolation of the voltages in a bipolar instrument, a distal clevis can be made of electrically insulating material and provide a separator between opposite polarity jaws that share a common pivot axis. Additionally, cables with non-conductive portions can be attached to the jaws using a high friction path. Use of a high friction path can simplify instrument assembly and avoid the need to employ a crimp or similar structure that may be difficult to reliably attach to non-conductive cable material.

In accordance with yet another aspect of the invention, the four drive cables of a wrist mechanism connect to three motor-driven axes in a backend mechanism. The backend mechanism works cooperatively with the wrist mechanism to achieve robotic control of the pitch, yaw, and grip of the effector. One embodiment of the backend mechanism uses two capstans, each with two cables wrapped about the capstan so that rotation of the capstan pulls in a length of one cable and reels out the same length of the other cable, and two robotic motorized degrees of freedom drive the capstans. The third degree of freedom is achieved from routing the cables through a set of pulleys, where the set of pulleys is configured to move as a group in proportion to a third robotic motorized degree of freedom. The motion of the group of pulleys is predominantly toward one capstan while away from the other, which has the effect of lengthening or feeding out one capstan's cable pair while shortening or pulling in the other pair of cables.

Another embodiment of the backend mechanism has two or more of the drive cables attached to the ends of respective levers. Gear mechanisms can move the cables by moving the ends of the levers opposite to the attachment of the cables or moving the respective pivots of the levers. With a proper arrangement of the pivots of the levers, motion of any one cable can be matched by an equal and opposite motion of one or more of the other cables, and the cable connections can ensure that cable tension is maintained during all wrist motions, including motion possible when the instrument is separated from robotic control. The levers generally pull the cables along the instrument's length. This near linear motion also allows cables to be replaced by solid rods or tubes that may be less costly that stranded cable.

FIG. 1 shows an example of a robotically controlled system 100 capable of using a medical instrument in accordance with an embodiment of the present invention. System 100, which may, for example, be a da Vinci® Surgical System available from Intuitive Surgical, Inc. includes multiple medical instruments 150, each of which is mounted in a docking port on a robotic arm 130. Instruments 150 can be made interchangeable, so that the instruments 150 mounted on arms 130 can be selected for a particular medical procedure or changed during a medical procedure to provide the clinical functions needed. As is well known in the art, instruments 150 can implement many functions including but not limited to forceps or graspers, needle drivers, and scissors of many different shapes and sizes. In accordance with an aspect of the current invention, an instrument 150 can be a bipolar cautery instrument.

The docking ports generally include drive motors that provide mechanical power for operation of instruments 150. The docking ports may additionally include an electrical interface for communication with instruments 150, for example, to identify the type of instrument in the docking port and to access parameters of the instrument. The electrical interface may also convey measurements such as measurements of the impedance of tissue, for example, for determination of parameters of a sealing operation. High voltage electrical systems (not shown) such as generators for cauterizing or sealing instruments would typically connect to instruments 150 through separate connectors but could alternatively be provided through built-in circuits in control system 100.

Each instrument 150 generally includes a transmission or backend mechanism 120, a main tube 110 extending from the backend mechanism 120, and a wrist mechanism 200 at the distal end of the main tube 110. Drive cables and electrical conductors that are connected to wrist mechanism 200 in an instrument 150 may extend through main tube 110 and connect to backend mechanism 120. Backend mechanism 120 typically provides a mechanical coupling of the drive cables to motorized axes provided by drive motors in control system 100. Control system 100 can thus control movement and tension in the drive cables as needed to position, orient, and operate wrist mechanism 200. A processing system 140 of system 100 can provide a doctor or other operating room personnel with a user interface enabling manipulation of arms 130. For example, an arm 130 can be used to insert the end of a medical instrument 150 through a cannula in small incisions in a patient undergoing a medical procedure and to operate wrist mechanism 200 at a worksite inside the patient. Accordingly, the diameter of wrist mechanism 200 and main tube 110 may be selected according to the size of the cannula with which the instrument will be used. In an exemplary embodiment, wrist mechanism 200 and main tube 110 are about 5 mm or about 8 mm in diameter to match the sizes of some existing cannula systems.

Main tube 110 is hollow and may contain both drive cables and electrical conductors that run from backend mechanism 120 to wrist mechanism 200. Main tube 110 may be rigid or flexible. A flexible main tube 100 would be used, for example, for insertion through an endoscope or other guide or cannula that follows a natural lumen or otherwise curved path. However, many common types of minimally invasive medical procedures such as laparoscopic surgery employ straight cannulas for insertion and removal of instruments, permitting use of a rigid main tube 110. A rigid main tube 110 can provide a more solid base for use of wrist mechanism 200 during a medical procedure. A rigid and straight main tube 110 also permits portions of drive cables extending through main tube 110 to be structures such as rods or tubes (e.g., hypotubes) that may provide better immunity to stretching or be less expensive.

Figure 2A:
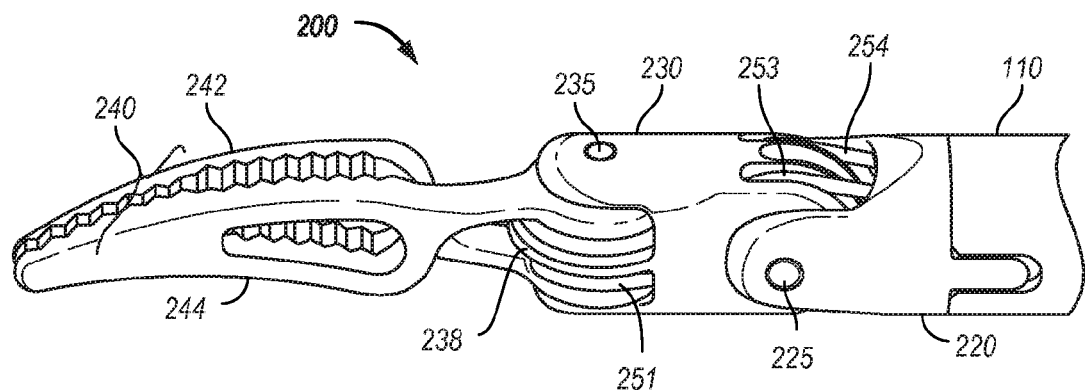
FIGS. 2A, 2B, and 2C show a wrist mechanism in accordance with an embodiment of the invention using a pair of devises and four drive cables that slide on guide surfaces integrated into the clevises.
Figure 2B:
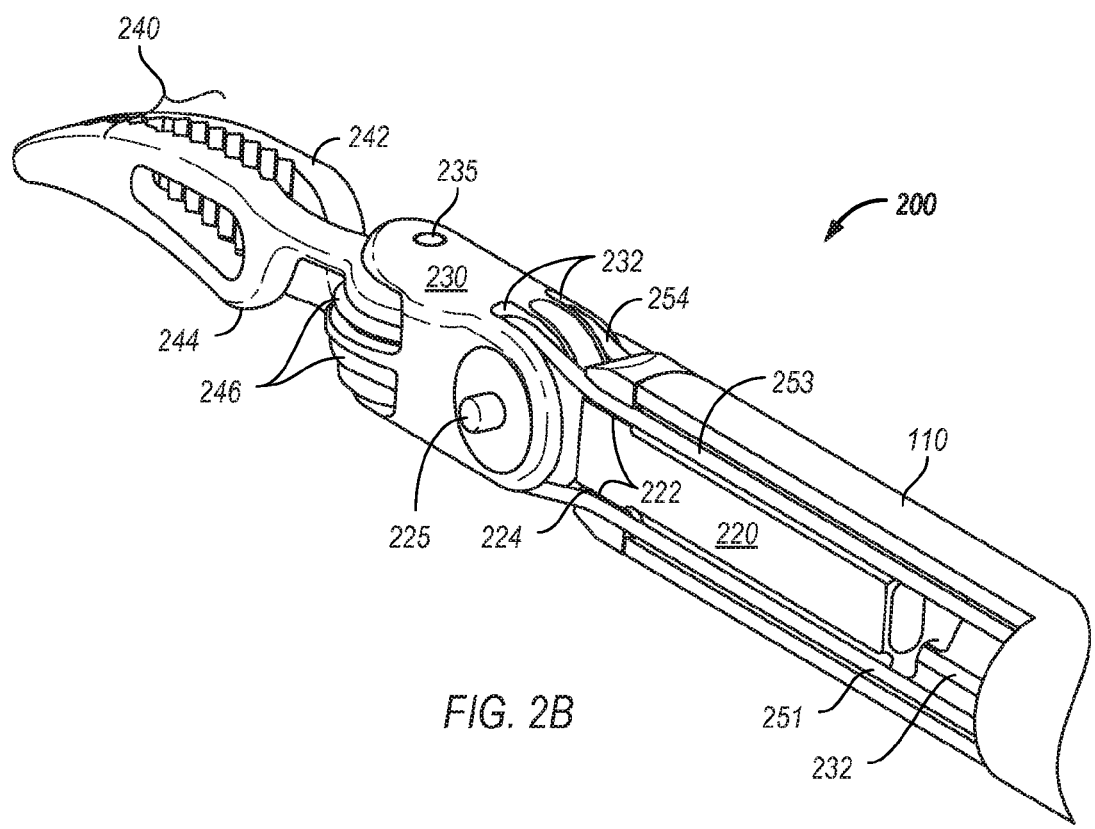
Figure 2C:
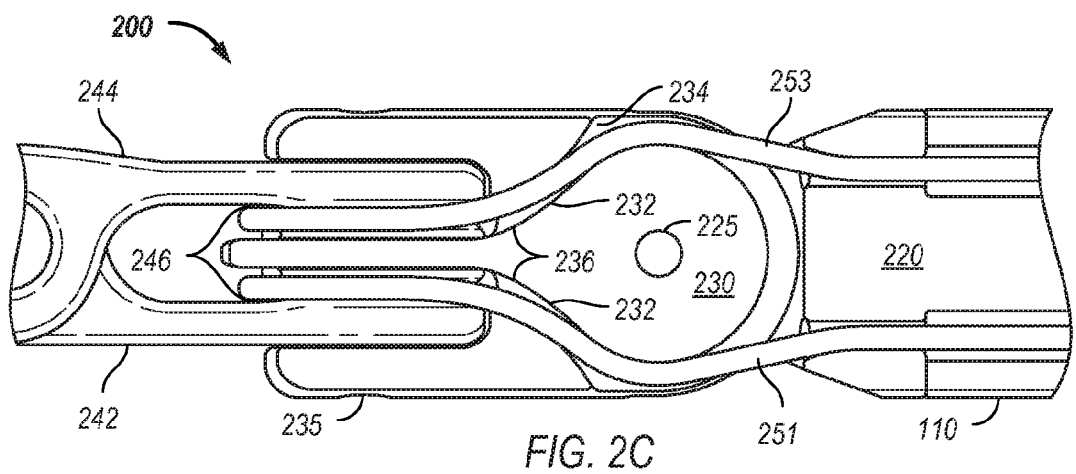

FIGS. 2A, 2B, and 2C show three views of a wrist mechanism 200 in accordance with an embodiment of the invention. As illustrated in FIG. 2A, wrist mechanism 200 includes a proximal clevis 220, a distal clevis 230, and an effector 240. Effector 240 includes jaws 242 and 244, each having a grip portion attached to a circular hub. Cables 251, 252, 253, and 254 are attached to effector 240, extend along solid surfaces of guide channels in effector 240, distal clevis 230, and proximal clevis 220, and from there extend back through main tube 110 to a backend mechanism (e.g., backend mechanism 120 of FIG. 1). The low part count of wrist mechanism 200 and the small number of drive cables 251, 252, 253, and 254 employed facilitate implementation of a small diameter for wrist mechanism 200 and main tube 110. Additionally, the low part count allows cost effective use of wrist mechanism in a single-use instrument, i.e., an instrument that is disposed of after a single medical procedure, instead of being an instrument that must be sterilized for subsequent use.

The partial cutaway view of wrist mechanism 200 in FIG. 2B shows how proximal clevis 220 can extend into and attach to main tube 110. A pin 225 in proximal clevis 220 attaches distal clevis 230 to proximal clevis 220 but allows distal clevis 230 to rotate about a pivot axis (sometimes referred to herein as the pitch axis) defined by pin 225. Proximal clevis 220 includes guide channels 222 for cables 251, 252, 253, and 254, and openings 224 of the guide channels 222 provide a range of motion for cables 251, 252, 253, and 254 that directs cables 251, 252, 253, and 254 into guide channels 232 of proximal clevis 230. In an exemplary embodiment, openings 224 of guide channels 222 are narrow in the direction parallel to pin 225 in order to direct cables 251, 252, 253, and 254 into respective guide channels 232 in distal clevis 230 but fan out in a direction perpendicular to pin 225 to keep cable friction low over the range of pitch angles that wrist mechanism 200 provides for distal clevis 230. Similarly, openings 234 of guide channels 232 nearest proximal clevis 220 are narrow in a direction parallel to the pitch axis and pin 225 but fan out in a direction perpendicular to pin 225 to accommodate pitch rotations and avoid pinching cables 251, 252, 253, and 254.

Guide channels 232 in distal clevis 230 define a radius about pin 225 at which cables 251, 252, 253, and 254 act on distal clevis 230 when rotating distal clevis 230 about pin 225, i.e., about the pitch axis. In order for the moment arm of the torque applied by the cables to be constant throughout the range of pitch motion of wrist mechanism 200, guide channels 232 have surfaces approximately in the shape of circular arcs. When distal clevis 230 is in the position illustrated in FIG. 2C, cable 253 has a portion that rests against a lower guide surface subtending a circular arc about the pitch axis of pin 225, and the distance between the pitch axis and the contact point of cable 253 on the lower surface of guide channel 232 is the moment arm for torque applied through cable 253. In the view of FIG. 2C, distal clevis 230 rotates clockwise when the backend mechanism pulls in cable 253. If clockwise rotation continues from the illustrated position, cable 253 will remain on the surface and act at a constant moment arm until distal clevis 230 reaches the limit of its range of motion. Further, through the entire motions, the surfaces of guide channels 232 that are circular arcs pull in and play out equal lengths of cable as distal clevis 230 rotate, thereby avoiding cable slack.

The cross-section of distal clevis 230 in FIG. 2C further illustrates how guide channels 232 extend through distal clevis 230 and direct cables 251, 252, 253, and 254 into circular guide channels 246 that are integrated into jaws 242 and 244 of effector 240. In particular, four guide channels 232 tunnel through distal clevis 230 for the four cables 251, 252, 253, and 254. Openings 236 of guide channels 232 nearest effector 240 direct cables 251, 252, 253, and 254 into respective guide channels 246 in jaws 242 and 244.

A pin 235 in distal clevis 230 is perpendicular to pin 225 and defines a pivot axis, sometimes referred to as the yaw axis or grip axis, for effector 240 as a whole or jaws 242 and 244 individually. (The yaw axis and the grip axis coincide in wrist mechanism 200.) Guide channels 246 of jaws 242 and 244 are circular and centered on pin 235, so that the radius of channels 246 is the moment arm for torques that cables 251, 252, 253, and 254 apply to jaws 242 and 244 when rotating jaws 242 and 244 or when maintaining a gripping force of jaws 242 and 244. The term gripping is used herein in a general sense since the action of jaws 242 and 244 depend on the work tips of jaws 242 and 244. In the illustrated embodiment of FIG. 2A, 2B, and 2C, the working tips of jaws 242 and 244 have a surface for gripping and may be used, for example, in forceps or cautery applications. Alternatively, "gripping," which closes jaws 242 and 242, may be a cutting action when the tips of jaws 243 and 244 are blades that cooperatively cut as a scissors. Gripping can thus perform different functions depending on the nature of effector 240.

The paths of cables 251, 252, 253, and 254 through wrist mechanism 200 do not employ pulleys. Instead of pulleys, wrist mechanism 200 guides cables 251, 252, 253, and 254 as described above using solid surfaces (i.e., the surfaces of guide channels 222 and 232) that are integral to devises 220 and 230. At some points, the guiding surfaces cradle opposing sides of the cable. For example, top and bottom surfaces of cable 253 as shown in FIG. 2C contact guide surface 232 at an inflection point 237 where the curvature of cable 253 changes. The solid guide surfaces are also curved to eliminate the need for large cable wrap angles and to maintain a fixed cable radius or moment arm. Large wrap angles were necessary in some prior wrist mechanisms to maintain a constant cable radius about the pivot axis throughout the range of motion. The surfaces of guide channels 222 and 232 can additionally be shaped to retain (or avoid derailment of) cables 251, 252, 253, and 254 and to keep cables 251, 252, 253, and 254 within the diameter constraint of a cannula through which wrist mechanism 200 passes during a minimally invasive medical procedure.

Guiding cables 251, 252, 253, and 254 experience less friction when compared to wrist mechanisms with larger cable wrap angles. Friction of cables 251, 252, 253, and 254 against distal clevis 230 and elsewhere may also be reduced through selection of the materials used. In particular, distal clevis 230 can be made of a plastic that provides low friction against the material of cables 251, 252, 253, and 254. Additionally, in some embodiments, cables 251, 252, 253, and 254 include portions of stranded metal cable that may be swaged to provide smoother cable surfaces that lower friction. The reduced cable friction allows pulleys to be deleted while maintaining clinically acceptable forces, torques, and precision and fidelity of motion for wrist mechanism 200. Avoiding the use of pulleys reduces the space requirements of wrist mechanism 200, allowing wrist mechanism 200 to have a clinically beneficial smaller working volume. Eliminating pulleys also reduces the cost.

Cables 251 and 252 attach to jaw 242 of effector 240, and cables 253 and 254 attach to jaw 244 of effector 240. The attachment of cables 251 and 252 to jaw 242 is such that pulling in a length of one cable 251 or 252 while releasing the same length of the other cable 252 or 251 causes jaw 242 to rotate about pin 235. Similarly, the attachment of cables 253 and 254 to jaw 244 is such that pulling in a length of one cable 253 or 254 while releasing the same length of the other cable 254 or 253 causes jaw 244 to rotate about pin 235. Many techniques for attaching cables 251, 252, 253, and 254 could be employed. For example, in a typical attachment, cables 251 and 252 (or cables 253 and 254) are opposite end portions of a cable loop that extends around circular arc about pin 235 that guide channel 246 defines in jaw 242 (or 244), and an attachment can be created by a knot tied in or a crimp fastened on the loop and fit into a matching notch (not shown) in guide channel 246. However, reliably attaching a crimp to some cable materials, e.g., non-conductive cable materials can present challenges. To avoid crimping, the cable loop may terminate through a high-friction pathway in jaw 242 or 244, so that friction prevents cables 251, 252, 253, and 254 from slipping relative to jaws 242 or 244.

Figure 3A:
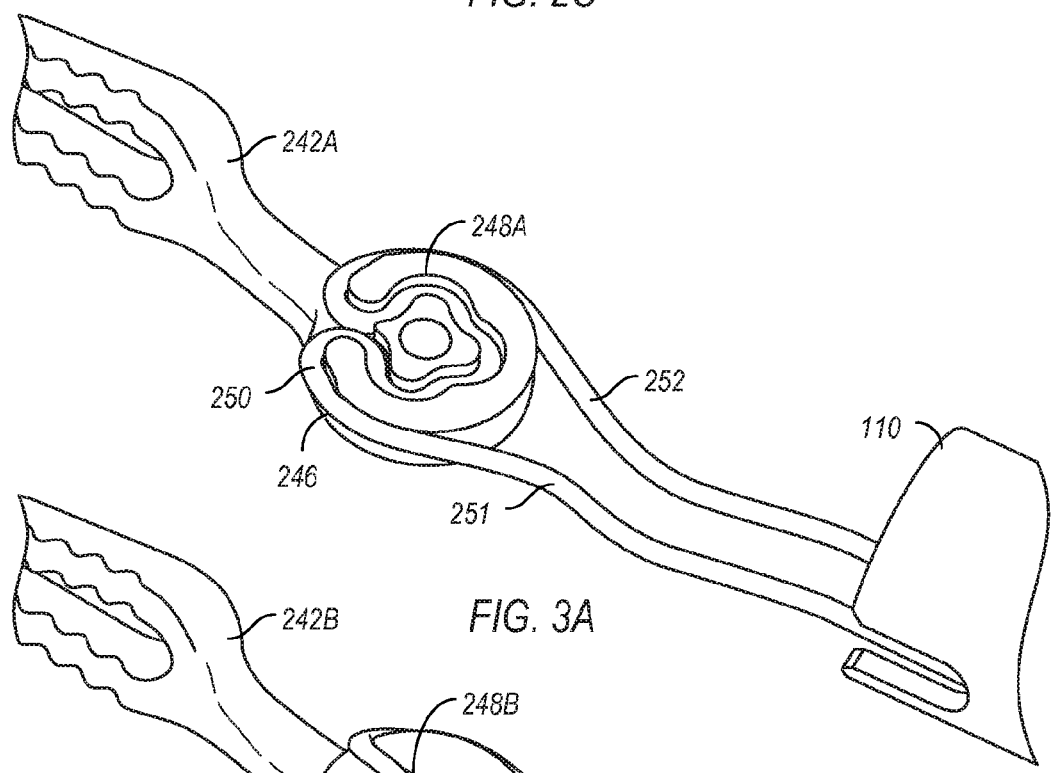
FIGS. 3A and 3B illustrate jaws with cables attached using high friction paths in accordance with alternative embodiments of the invention.

FIG. 3A shows a jaw 242A attached to a cable loop 250 having portions that extend back into main tube 110 as to cables 251 and 252. Loop 250 extends along circular arcs of guide channel 246 of jaw 242A into a high friction path 248A, and back out along another circular arc of guide channel 246. Path 248A is substantially co-planar with guide channel 246 and includes multiple sharp bends. Contact between cable loop 250 and the surface of jaw 242A at the bends in path 248A creates friction that prevents or resists sliding of cable 250, each bend increasing the frictional force that acts to retain cable loop 250 against pullout. Cable loop 250 has no crimp attached.

Figure 3B:
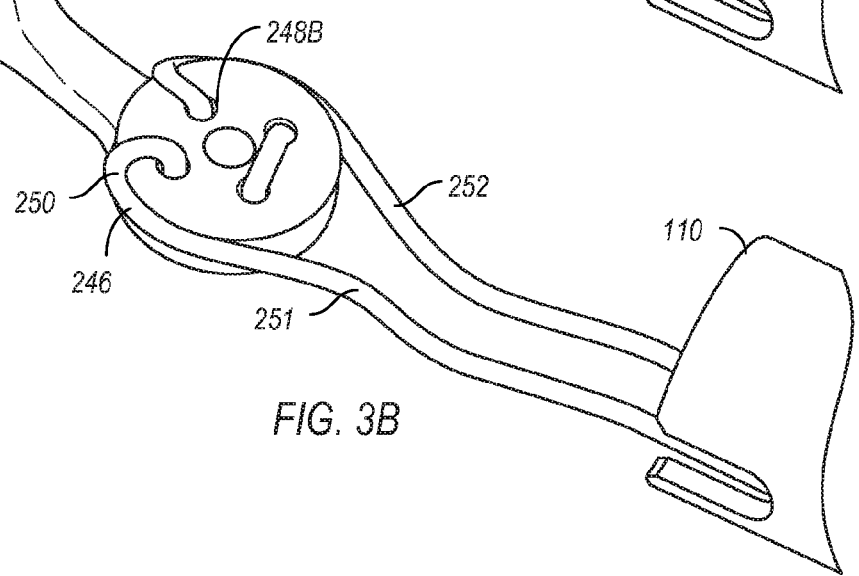

FIG. 3B shows a jaw 242B using an alternative high friction path 248B in which cable loop 250 is threaded through several holes in jaw 242B. Contact of cable loop 250 with jaw 242B at the bends in cable loop 248B (including at locations where cable loop 250 passes through jaw 242B) creates friction that resists or prevents sliding of cable loop 250. Accordingly, a crimp is not required to attach cable loop 250 to jaw 242B. Assembly of a wrist mechanism using high friction path 248B requires threading of cable through holes in jaw 242B, but once threaded, cable loop 250 is solidly retained in jaw 242B, which may make assembly of a wrist using high friction path 248B of FIG. 3B simpler than assembly of a wrist using high friction path 248A of FIG. 3A.

The jaw attachments without crimps eliminate the space requirement of crimps and the cost associated with crimping. The attachments without crimps are also advantageous for some cable materials (e.g. non-metallic cables) for which crimping can be troublesome. As described further below, non-metallic cables can be useful as electrical insulators in cauterizing instruments. Even instruments that do not require electrical insulation, non-metallic cables may provide reduced friction, wear, and particulate generation against mating surfaces in the wrist mechanism.

Figure 4A:
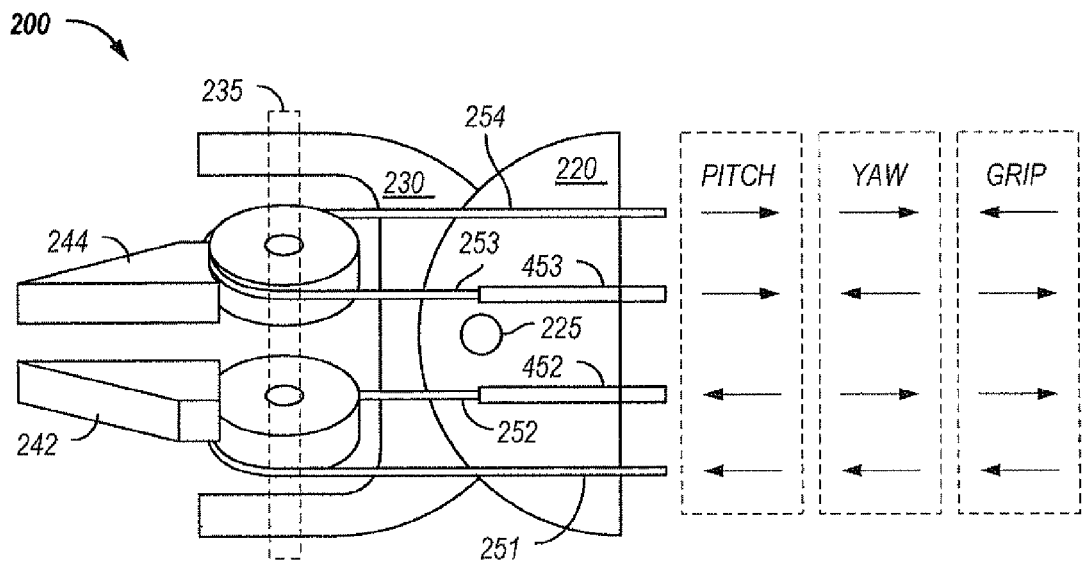
FIG. 4A illustrates the movements of four drive cables that produce changes in the pitch, yaw, and grip of a wrist mechanism in accordance with an embodiment of the present invention.
Figure 4B:
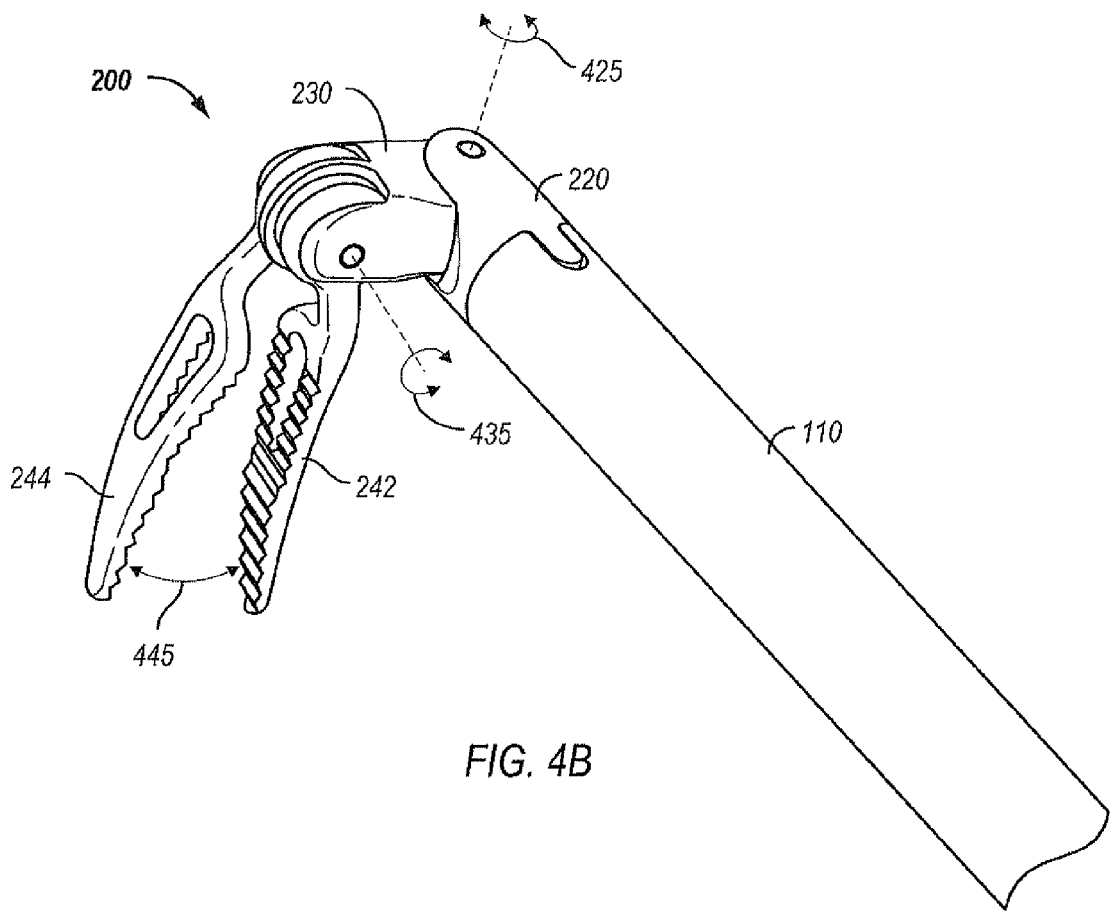
FIG. 4B shows a perspective view illustrating pivot axes of the wrist mechanism of FIGS. 2A, 2B, and 2C when operated using the cable movements of FIG. 4A.

Changing the pitch, yaw, or grip of the wrist mechanism 200 described above generally requires movements or actions respectively applied to four cables 251, 252, 253, and 254. FIG. 4A shows a simplified view of wrist mechanism 200 and illustrates processes for changing the pitch, yaw, and grip of jaws 242 and 244. The illustrated processes can generally be performed one at a time or simultaneously in any desired combination to change the pitch, yaw, and grip of mechanism 200. FIG. 4B shows wrist mechanism 200 in more detail to illustrate rotation axes of wrist mechanism 200 and is described here simultaneously with FIG. 4A.

Pitch axis rotations, i.e., rotations 425 in FIG. 4B, rotate distal clevis 230 about the pitch axis defined by pin 225. For clockwise rotation about the pitch axis, a backend mechanism (not shown) pulls in identical lengths of cables 253 and 254 while releasing the same lengths of cables 251 and 252. Cables 253 and 254 apply forces to distal clevis 230 at moment arms defined by the guide channels of cables 253 and 254 through distal clevis 230. Similarly, for counterclockwise rotation of clevis 230 about the pitch axis, the backend mechanism pulls in identical lengths of cables 251 and 252 while releasing the same lengths of cables 253 and 254.

Yaw rotations, i.e., rotations 435 in FIG. 4B, corresponds to both rotating jaws 242 and 244 in the same direction and through the same angle. In particular, the backend mechanism pulling in a length of cable 252 and releasing an equal length of cable 251 will cause jaw 242 to rotate in a clockwise direction about the axis of pin 235. For this rotation, the guide channel in jaw 242 defines the moment arm at which cable 252 applies a force jaw 242, and the resulting torque causes jaw 242 to rotate clockwise and cables 251 and 252 to slide on the solid surface of guide channels in distal clevis 230. If at the same time the backend mechanism pulls in a length of cable 254 and releases the same length of cable 253, jaw 244 will rotate clockwise through an angle that is the same as the angle through which jaw 242 rotates. Accordingly, jaws 242 and 244 maintain their positions relative to each other and rotate as a unit through a yaw angle. Counterclockwise rotation of the effector including jaws 242 and 244 is similarly accomplished when the backend mechanism pulls in equal lengths of cables 251 and 253 while releasing the same lengths of cables 252 and 254.

Grip rotations, i.e., rotations 445 in FIG. 4B, are achieved by rotating jaws 242 and 244 in opposite directions by the same amount. To open the grip of jaws 242 and 244, the backend mechanism pulls in equal lengths of cables 251 and 254 while releasing the same lengths of cables 252 and 253, causing jaws 242 and 244 to rotate in opposite directions away from each other. To close the grip of jaws 242 and 244, the backend mechanism pulls in equal lengths of cables 252 and 253 while releasing the same lengths of cables 251 and 254, causing jaws 242 and 244 to rotate in opposite directions toward each other. When faces of jaws 242 and 244 come into contact, the tension in cables 252 and 253 can be kept greater than the tension in cables 251 and 254 in order to maintain gripping forces.

FIG. 4A illustrates that portions 452 and 453 of cables 252 and 253, respectively, can be made stiffer or thicker than corresponding portions of cables 251 and 254 to accommodate the higher or maintained tensions used for gripping. This can be achieved by fusing the ends of cable loops corresponding to cable 252 or 253 with heavier material. In a typical embodiment of the invention, portions of cables 251, 252, 253, and 254 having larger flexing during cable movement can be made of a flexible material such as a stranded metal cable. Relatively straight portions of each cable (e.g., portions extending back through the main tube) in some embodiments can be less flexible material such as hypotubes or similar structures that have advantages in cost and immunity to stretching, and in such an embodiment, larger hypotubes can be used for portions 452 and 453 of cables 252 and 253. The effective stiffness of each of the four drive cables 251, 252, 253, and 254 can thus be controlled advantageously for improved clinical performance. In particular, the effective stiffness of drive cables 252 and 253 that cause jaws 242 and 244 to close is greater than the stiffness of drive cables 251 and 252 that cause jaws 242 and 244 to open. This arrangement minimizes cable slack, improving the fidelity of motion of wrist mechanism 200. Materials, diameters, and lengths (e.g., of portions 452 and 453) are controlled to affect desired stiffness. Not using the larger structures in cables 251 and 254 saves cost and space.

Figure 5A:
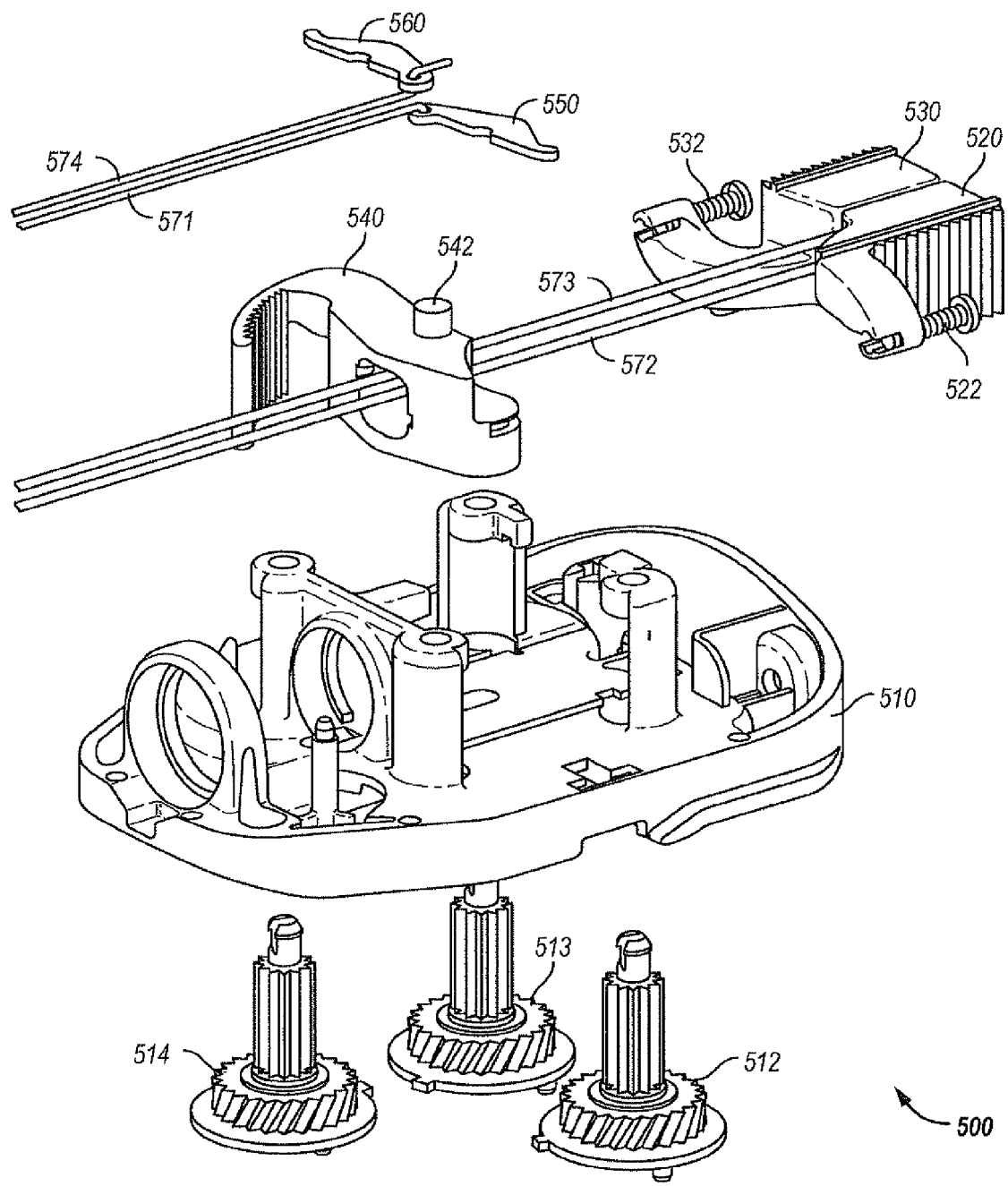
FIGS. 5A and 5B respectively show an exploded view and a cross-sectional view of a backend mechanism in accordance with an embodiment of the invention using gears and levers to move drive cables.

FIG. 5A shows an exploded view of a portion of a backend mechanism 500 in accordance with an embodiment of the invention predominantly employing gears and levers to control movement of a wrist mechanism. The illustrated portion of backend mechanism 500 includes a chassis 510, three drive shafts 512, 513, and 514, three toothed components 520, 530, and 540, and two levers 550 and 560 and couples to four drive cables 571, 572, 573, and 574. The components 510, 520, 530, 540, 550, and 560 can be made of any suitably durable material such as molded or machined plastic or metal depending on the required loads and tolerances of the individual components. As described further below, cables 571, 572, 573, and 574 can correspond to cables 251, 252, 253, and 254 and connect to a wrist mechanism of the type described above with reference to FIGS. 2A, 2B, and 2C. However, backend mechanism 500 can more generally be used in any instrument for which connection of four cables to three motor driven axes is desired.

Chassis 510 may have a footprint chosen for connection to a robotic control system containing motors that operate drive shafts 512, 513, and 514. In particular, chassis 510 may be shaped such that drive shafts 512, 513, and 514 when fit into chassis 510 are positioned to be engaged and rotated by a robotic control system such as the da Vinci® Surgical System.

Drive shaft 512 acts as a pinion that engages a rack portion of toothed component 520. Toothed component 520 is attached to cable 572 and moves in a straight line to pull in or release a length of cable 572 as drive shaft 512 turns. Toothed component 520 also includes an arm containing an adjustment screw 522 that contacts lever 550. In particular, adjustment screw 522 contacts lever 550 at an end opposite to where cable 571 attaches to lever 550. A pivot point or fulcrum for lever 550 is on toothed component 540 that acts as a rocker arm as described further below. In operation, as toothed component 520 moves, adjustment screw 522 causes or permits rotation of lever 550 about the pivot point so that lever 550 can pull in or release cable 571. The connection of cable 571 to lever 550 and the contact point of adjustment screw 522 on lever 550 can be made equidistant from the pivot point of lever 550, so that when toothed component 520 pulls in (or releases) a length of cable 572, lever 550 releases (or pulls in) the same length of cable 571. Adjustment screw 522 permits adjustment of the tension in cables 571 and 572 by controlling the orientation of lever 550 relative to the position of toothed component 520.

Drive shaft 513 similarly acts as a pinion that engages a rack portion of toothed component 530. Toothed component 530 is attached to drive cable 573 and moves in a straight line to pull in or release a length of cable 573 as drive shaft 513 turns. Toothed component 520 also includes an arm containing an adjustment screw 532 that contacts lever 560 at an end opposite to where cable 574 attaches to lever 560. A pivot point or fulcrum for lever 560 is on toothed component 540, and the distance of the connection of cable 574 from the pivot point of lever 560 can be made the same as the distance from the pivot point of lever 560 to the contact point of adjustment screw 532 on lever 560. As a result, when toothed component 550 pulls in (or releases) a length of cable 573, lever 560 releases (or pulls in) the same length of cable 574. Adjustment screw 523 permits adjustment of the tension in cables 573 and 574 by controlling the orientation of lever 560 relative to the position of toothed component 530.

Drive shafts 512 and 513 can be operated to change the yaw angle or the grip of a wrist mechanism using the processes described above. For example, when cables 571, 572, 573, and 574 respectively correspond to cables 251, 252, 253, and 254 of FIG. 4A, turning drive shafts 512 and 513 at the same speed in the same direction or in opposite directions will change the grip or yaw of wrist mechanism 200.

Drive shaft 514 engages an internal sector gear portion of toothed component 540. Toothed component 540 has a pivot attached to chassis 510, so that as drive shaft 514 turns, toothed component 540 rotates about pivot 542. Toothed component 540 also includes protrusions (not visible in FIG. 5A) that act as pivot points for levers 550 and 560. These protrusions can be located equidistant from pivot 542, so that as toothed component 540 rotates one pivot moves closer to the wrist mechanism and the other pivot moves further from the wrist mechanism by an equal amount. If toothed components 520 and 530 are moved at the appropriate speeds and directions to maintain the orientations of levers 550 and 560, rotation of toothed component 540 will pull in (or release) equal lengths of cables 571 and 572 and release (or pull in) the same lengths of cables 573 and 574. Backend mechanism 500 can thus be used to perform a pitch change as described above with reference to FIG. 4A when cables 571, 572, 573, and 574 respectively correspond to cables 251, 252, 253, and 254, but the pitch change process requires coordinated rotations of all three gears 512, 513, and 514. Such coordinated rotations can be implemented in software of a robotic control system.

Figure 5B:
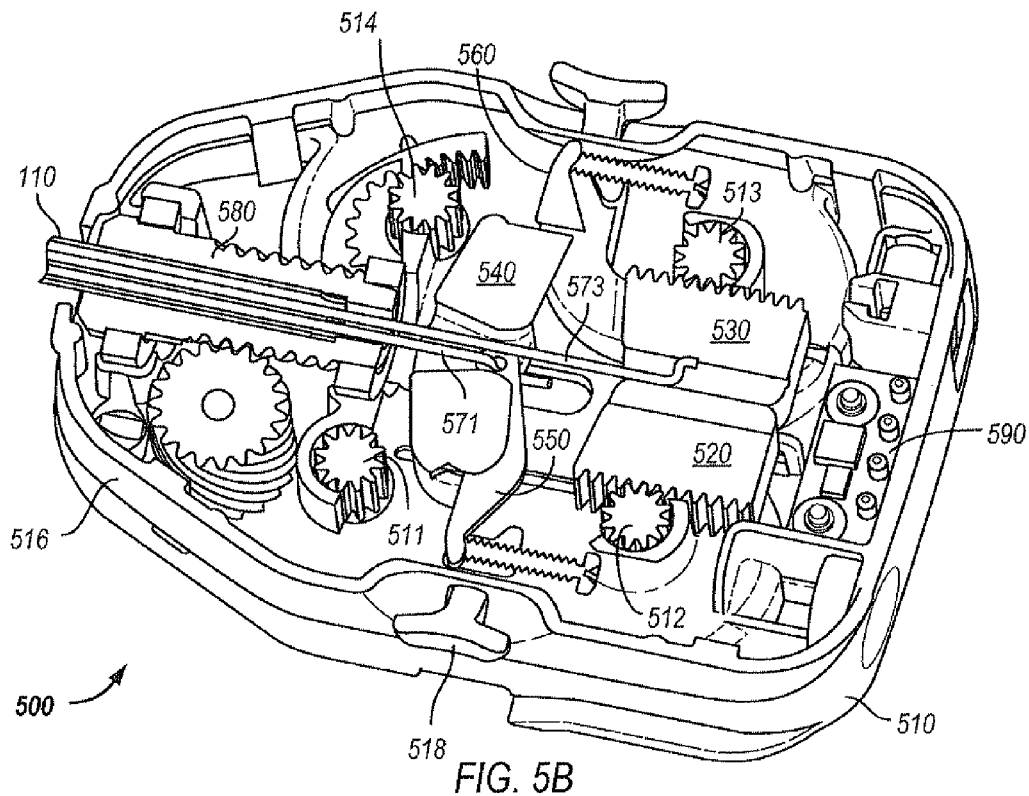

FIG. 5B shows a cross-sectional view of backend mechanism 500 when assembled with additional components not shown in FIG. 5A. As illustrated, backend mechanism 500 includes drive shafts 512, 513, and 514 that respectively engage toothed components 520, 530, and 540, and a robotic control system coupled to backend 500 can rotate drive shafts 512, 513, and 514 to control the pitch, yaw, and grip of a wrist mechanism (not shown). Cables 571, 572, 573, and 574 extend from the wrist mechanism (not shown) at a distal end of a main tube 110, through main tube 110 and into backend mechanism 500.

Main tube 110 is attached in backend mechanism 500 to a helical gear 580, which is coupled to a drive shaft 511 through an intervening helical gear 582. When a control system rotates drive shaft 511, helical gears 582 and 580 rotate main tube 110 and thereby change the roll angle of the effector at the distal end of main tube 110.

FIG. 5B also shows a circuit board 590, which may be included in backend mechanism 500 for electrical connection to a robotic control system. Circuit board 590 can include memory or other circuitry that sends an identification signal to the control system to indicate which instrument is connected to the control system and/or to provide key parameters that the control system may need for proper operation of the instrument. Connection to electrical components of the effector, e.g., to energize a cauterizing instrument or to relay sensor measurements, could be in circuit board 590. However, a separate electrical connection may be desired for energizing the effector, particularly when high voltages are required.

Backend mechanism 500 as illustrated in FIG. 5B also includes a cover 516 that encloses mechanical and electrical components of backed mechanism 500. Two levers 518 can be used to disengage backend mechanism 500 from a robotic control system.

Figure 6:
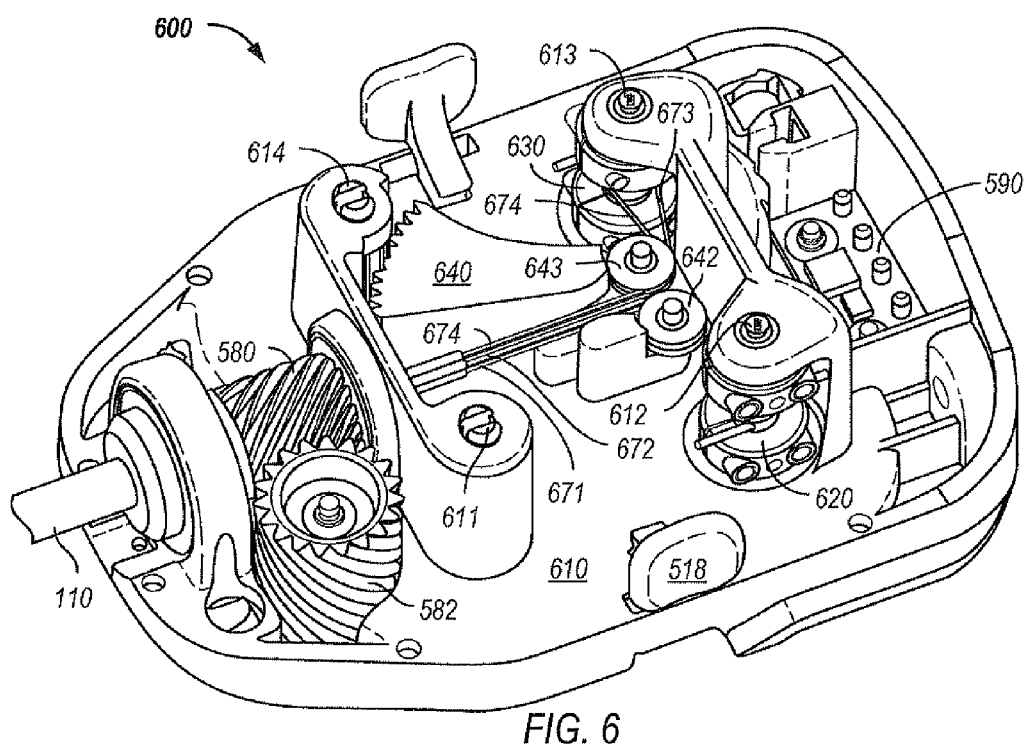
FIG. 6 shows a backend mechanism in accordance with an embodiment of the invention using pulleys, capstans, and gears to move drive cables.

Pulleys and capstans can be used in a backend mechanism in place of some toothed components of FIGS. 5A and 5B. FIG. 6 shows a backend mechanism 600 in accordance with an embodiment of the invention employing cables, pulleys, and capstans. Backend mechanism 600 includes a chassis 610, four drive shafts 611, 612, 613, and 614, a pair of capstans 620 and 630, a rocker arm 640 on which a first pair of pulleys 642 and a second pair of pulleys 643 are mounted, helical gears 580 and 582, and a circuit board 590. Four drive cables 671, 672, 673, and 674, which are connected to a wrist mechanism (not shown), extend through a main tube 110 into backend mechanism 600. Cables 671, 672, 673, and 674 can respectively correspond to cables 251, 252, 253, and 254, which are connected to wrist mechanism 200 of FIGS. 2A, 2B, and 2C. However, backend mechanism 600 can more generally be used in any instrument for which connection of four cables to three motor driven axes is desired.

The shape of chassis 610 is generally selected to have a footprint corresponding to a mounting on a robotic control system. Backend mechanism may thus be fitted to a control system so that drive shafts 611, 612, 613, and 614 are mechanically coupled to motors in the control system. The control system is then able to rotate drive shafts 611, 612, 613, and 614 through precise angles that may be selected by software to achieve the desired operation or movement of the instrument.

Cables 671 and 672 pass from main tube 110, wind around one or more pulleys 642, and wrap around capstan 620. The wrapping of cables 671 and 672 around capstan 620 is such that when capstan 620 turns, a length of one cable 671 or 672 is pulled in and an equal length of the other cable 672 or 671 fed out. Similarly, cables 673 and 674 pass from main tube 110, wind around one or more pulleys 643, and are wrapped around capstan 630, so that when capstan 630 turns a length of one cable 673 or 674 is pulled in and an equal length of the other cable 674 or 673 is fed out. Drive shafts 612 and 613 are respectively coupled to turn capstan 620 and 630. A control system can thus turn drive shafts 612 and 613 to change the yaw angle or the grip of a wrist mechanism using the processes described above. For example, when cables 671, 672, 673, and 674 respectively correspond to cables 251, 252, 253, and 254 of FIG. 4A, turning drive shafts 612 and 613 at the same speed in the same direction or in opposite directions will change the grip or yaw of wrist mechanism 200.

Pulleys 642 and 643 are mounted on rocker arm 640. Rocker arm 640 has a sector gear portion that engages drive shaft 614 and is coupled to chassis 610 to rotate or rock about a pivot axis when drive shaft 614 turns. The sector gear portion and pivot of rocker arm 640 are designed so that rotation of rocker arm 640 primarily causes one set of pulleys 642 or 643 to move toward its associated capstan 620 or 630 and the other set of pulleys 643 or 642 to move away from its associated capstan 630 or 620. This effectively pulls in lengths of one pair of cables 671 and 672 or 673 and 674 and releases an equal length of the other pair of cables 673 and 674 or 671 and 672. Backend mechanism 600 simply through rotation of drive shaft 614 can thus change the pitch in a wrist mechanism as described above with reference to FIG. 4A when cables 671, 672, 673, and 674 respectively correspond to cables 251, 252, 253, and 254.

Backend mechanism 600 can control the roll angle of a wrist mechanism at the distal end of main tube 110 using drive shaft 611 to turn helical gears 582 and 580. Helical gears 580 and 581 are coupled to main tube 110 and operate in the same manner as described above.

Cables 671, 672, 673, and 674 in backend mechanism 600 wind or wrap around pulleys 642 and 643 and capstans 620 and 630 and must be able to flex when capstans 620 and 630 rotate. Accordingly, portions of cables 671, 672, 673, and 674 in backend mechanism 600 require flexibility and may be, for example, stranded metal cable that can be flexed repeatedly around relatively sharp turns without damage. Accordingly, each cable 671, 672, 673, and 674 may include three portions, a stranded cable portion in the wrist mechanism, a more rigid portion (e.g., hypotube) extending through the straight portion of main tube 110, and a second stranded cable portion in backend mechanism 600. For comparison, backend mechanism 500 of FIG. 5B moves cables 571, 572, 573, and 574 in nearly linear motions and does not require significant flexing of cables 571, 572, 573, and 574 around pulleys or other sharp bends. Accordingly, the potions of cables 571, 572, 573, and 574 in backend mechanism 500 can be relatively rigid structures such as hypotubes.

Backend mechanism 600 of FIG. 6 like backend mechanism 500 of FIG. 5B includes a circuit board 590 with circuits that provide an interface to a robotic control system as described above. High voltage connections are generally made through separate electrical connections and wires that may be run through backend mechanism 500 or 600 and run through main tube 110 to the effector. For example, in one embodiment of the invention, the instrument is a bipolar cautery instrument and electrical wires or other electrical conductors (not shown) connect to a generator through connectors (not shown) on the back end mechanism and from there run with the drive cables through main tube 110 to the wrist mechanism at the distal end of main tube 110. At the wrist mechanism, electrical energy for cautery can be delivered through contacts, which engage jaws in the effector much the same manner as brushes in a motor.

Figure 7A:
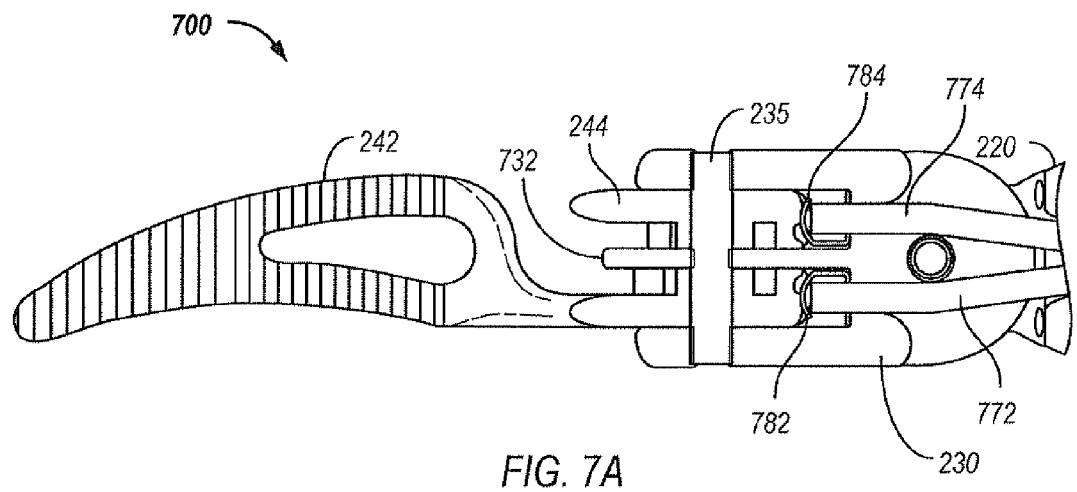
FIG. 7A is a cross-sectional view of a wrist mechanism in a bipolar cautery instrument having electrical connections using brush type contacts in accordance with an embodiment of the invention.
Figure 7B:
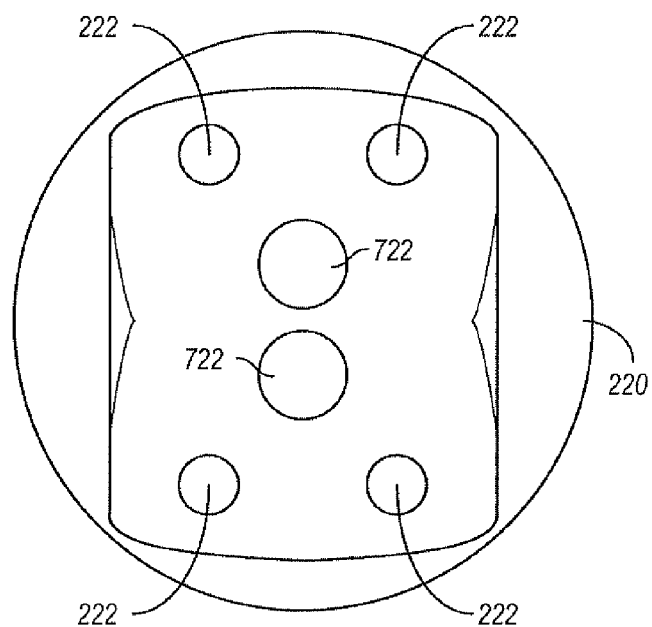
FIG. 7B illustrates one arrangement of guides for drive cables and electrical conductors in a bipolar cautery instrument in accordance with an embodiment of the invention.

FIG. 7A shows a cross-sectional view of a wrist mechanism 700 for a cautery instrument. Wrist mechanism 700 includes a proximal clevis 220, a distal clevis 230 rotatably attached to a pin 225 through proximal clevis 220, and jaws 242 and 244 rotatably attached to a pin 235 through distal clevis 230. Drive cables (not shown in FIG. 7A) for wrist mechanism 700 can follow guide channels in clevis 220 and 230 and attach to jaws 242 and 244 as described above with reference to FIGS. 2A, 2B, and 2C and can change the pitch, yaw, and grip of wrist mechanism 700 in the same manner described with reference to FIGS. 4A and 4B. The drive cables or at least the portion of the drive cables that contact jaw 242 or 244 are preferably made of an insulating material. As mentioned above with reference to FIGS. 3A and 3B, the attachment of drive cables to jaws 242 and 244 can be made using high friction paths to avoid difficulties that may arise from crimping of non-conductive cables. Insulated electrical wires or other conductors 772 and 774 also feed through proximal clevis 220 and distal clevis 230 so that ends of wires 772 and 774 are respectively adjacent to jaws 242 and 244. FIG. 7B shows an end view of proximal clevis 220 illustrating how guide channels 222 for the drive cables can be positioned near an outer edge of proximal clevis 220 to provide room near the center axis of proximal clevis 220 for conduits 722. Wires 772 and 774 can thus be run through devises 220 and 230 without interfering with the drive cables.

Contacts 782 and 784 as shown in FIG. 7A are at the end of wires 772 and 774 and in electrical contact with respective jaws 242 and 244. Contacts 782 and 784 can be made of tempered or spring metal that is compressed to make good electrical contact with jaws 242 and 244 when jaws 242 and 244 are assembled into distal clevis 230. In illustrated embodiment, contacts 782 and 784 engage a constant-radius circumference at the proximal ends of respective jaws 242 and 244, so that as jaws 242 or 244 rotate during a change of yaw angle or grip, contacts 782 and 784 remain in contact with the circular surface. Alternatively, both or either contact 782 and 784 could be positioned to engage a flat side of jaw 242 or 244 perpendicular to the grip axis and pin 235. An advantage of contacts 782 and 784 is a reduction in the motion imparted to wires 772 and 774. In particular, wires 772 and 774 move only during pitch changes but not when the yaw or grip is being changed. With a direct (e.g., soldered or crimped) electrical contact, attached wires move whenever the pitch, yaw, or grip changes. The reduction in movement of wires 772 and 774 reduces the likelihood of damage to wires 772 and 774 from fatigue, contact with a foreign object, kinking, or wear.

Contacts 782 and 784 can be used to electrically energize jaws 242 and 244 with opposite polarity voltages to activate the cauterizing function of wrist mechanism 700. For example, for sealing of a vessel during a medical procedure, wrist mechanism 700 can be manipulated so that jaws 242 and 244 grip a vessel, thereby closing the vessel to be sealed. Conductors 772 and 774 and contacts 782 and 784 can then energize jaws 242 and 244 with high frequency AC signals having opposite polarity. While the electrical energy is applied to jaws 242 and 244, a current flows through the tissue gripped in jaws 242 and 244, and the duration of the electrical signal can be selected so that the current cauterizes the tissue and seals the gripped vessel. Cautery can also be used in other manners known in the art, for example, to cut or destroy tissue during a medical procedure.

As is known in the art, power for electrocautery is generally from a high voltage (e.g., above about 250 volts) AC signal having a frequency above about 100 kHz. To avoid unintended tissue damage, each electrical signal needs to be isolated from any unintended contact with a patient and correspondingly isolated from contact with any exposed portion of the instrument other than jaws 242 and 244. A coating on wires 772 and 774 insulates the signal from the main tube and proximal clevis 220 so that neither is electrically energized. Wires 772 and 774 are preferably stranded for flexibility and have an insulating coating of a material such as FEP, which provides a relatively high dielectric constant and low friction when a wire 772 or 774 move. Distal clevis 230, in which contacts 782 and 784 reside, can be made out of an insulating material such as plastic (e.g., Ultem) or an insulating ceramic. Similarly, pin 235, which is in contact with both jaws 242 and 244, is made of an insulating material such as a ceramic to avoid voltage leakage and prevent shorting between jaws 242 and 244.

In the example of bipolar cautery instrument as illustrated in FIG. 7A, jaws 242 and 244 are positioned in cavities in insulating distal clevis 230. In particular, a separator 732 is integrated in distal clevis to provide electrical isolation between the opposite polarity jaws 242 and 244. The cavities can provide sufficient isolation distance between jaws 242 and 244, such that hermetic seals or separate encapsulation of each jaw 242 or 244 (as done in some prior cautery systems) is not required. Contacts such as 782 and 784 could also be used in a monopolar cautery where both jaws 242 and 244 are at the same voltage, but separation between jaws 242 and 244 is not required for monopolar cautery.

Many of the above described embodiments can reduce the cost of a minimally invasive surgical instrument by reducing: the number of parts in the instrument; the complexity of the instrument; the cost of the materials used; the manufacturing difficulty of the parts; and the difficulty of the assembly of the instrument. Reducing cost has obvious benefits, but also enables the creation of single-use instruments that are cost competitive (per case) when compared against existing reusable instruments. A single-use instrument has further benefits of eliminating reprocessing/sterilization at the hospital and allows further cost saving during manufacture of the instruments because components do not need to be designed and verified for reprocessing.

Embodiments of the invention that reduce the parts count can also enable production of smaller instruments. This has clinical benefit by decreasing both the diameter and length of the wrist. Medical procedures may thus be able to use smaller incisions, and greater control of precision wrist manipulations may be possible. For example, a bipolar endowrist cautery instrument may be fabricated with a 5-m diameter, while previously, such instruments were only manufactured with a diameter 8-mm or larger.

Although the invention has been described with reference to particular embodiments, the description is only an example of the invention's application and should not be taken as a limitation. Various adaptations and combinations of features of the embodiments disclosed are within the scope of the invention as defined by the following claims.

What is claimed is:

1. A cauterizing instrument comprising:
   a clevis;
   a first jaw having a hub that is mounted on the clevis to permit rotation of the first jaw about a pivot axis of the clevis;
   a first electrical conductor; and
   a first contact on the first electrical conductor making electrical contact with a constant-radius circumferential edge of the hub, wherein the first contact presses on the circumferential edge perpendicularly to the pivot axis and slides on the circumferential edge when the first jaw rotates.

2. The instrument of claim 1, further comprising:
   a first cable attached to the first jaw so that pulling on the first cable causes the first jaw to rotate about a pin in the clevis, wherein the first cable is made of an insulating material and the pin defines the pivot axis.

3. The instrument of claim 2, wherein the first cable follows a high friction path in the first jaw, and is attached to the first jaw in that frictional forces resist sliding of the first cable relative to the first jaw.

4. The instrument of claim 2, further comprising:
a main tube, wherein the jaw and the clevis are at a distal end of the main tube and the first cable extends through the main tube; and
a backend mechanism coupled to a proximal end of the main tube, wherein the backend mechanism is operable to move the first cable for the actuation of the first jaw, and the backend mechanism provides a mechanical coupling of the first cable to a drive motor provided in a docking port of a control system.

5. The instrument of claim 2, further comprising a second cable attached to the first jaw so that pulling on the second cable causes the first jaw to rotate about the pin in a direction that is opposite a direction of rotation of the first jaw that results from pulling on the first cable.

6. The instrument of claim 5, wherein the first cable and the second cable are opposite ends of a cable loop that passes through a high friction path in the first jaw.

7. The instrument of claim 6, wherein the high friction path is perpendicular to the pivot axis and includes a plurality of bends.

8. The instrument of claim 6, wherein the cable loop is threaded through the high friction path which comprises a plurality of holes through the first jaw.

9. The instrument of claim 1, wherein the clevis is made of an electrically insulating material, wherein and the first jaw is mounted on a pin of the clevis.

10. The instrument of claim 9, further comprising:
a second jaw mounted on the pin of the clevis;
a second electrical conductor passing through the clevis; and
a second contact on the second electrical conductor making electrical contact with a surface of the second jaw, wherein the second contact slides on the surface of the second jaw when the second jaw rotates.

11. The instrument of claim 10, wherein the first electrical conductor is connected to conduct a first electrical signal and the second electrical conductor is connected to conduct a second signal that has a polarity that is opposite to a polarity of the first signal.

12. The instrument of claim 11, wherein the clevis comprises a separator that is between the first and second jaws and electrically isolates the first jaw from the second jaw.

13. The instrument of claim 11, wherein the clevis comprises a first cavity in which an end of the first jaw resides and a second cavity in which an end of the second jaw resides.

14. The instrument of claim 1, wherein the first contact comprises a spring structure that is compressed against the circumferential edge of the hub of the first jaw.

15. The instrument of claim 1, wherein a portion of the first electrical conductor extends through a conduit formed in the clevis.

16. A medical instrument comprising:
a backend mechanism;
a main tube extending from the backend mechanism;
a clevis that is made of an insulating material and rotatably mounted at a distal end of the main tube;
first and second jaws connected to rotate about a pin of the clevis;
a first conductor extending through the main tube; and
a first contact on the first conductor making electrical contact with a circumferential edge of a hub of the first jaw, wherein the first contact presses on the circumferential edge perpendicularly to a pivot axis defined by the pin and slides on the circumferential edge of the hub when the first jaw rotates.

17. The instrument of claim 16, further comprising:
a second conductor extending through the main tube; and
a second contact on the second conductor making electrical contact with a surface of the second jaw, wherein the second contact slides on the surface of the second jaw when the second jaw rotates.

18. The instrument of claim 16, wherein the backend mechanism fits into a docking port of a control system that controls operation of the instrument.

19. The instrument of claim 16, wherein a portion of the first conductor extends through a conduit formed in the clevis.

20. A method of electrically energizing an effector in a medical instrument, comprising: providing said instrument with: a clevis; a first jaw having a hub that is mounted on the clevis to permit rotation of the first jaw about a pivot axis of the clevis; a first electrical conductor; and a first contact on the first electrical conductor making electrical contact with a constant-radius circumferential edge of the hub; pressing the first contact against the circumferential edge of the hub, wherein the pressing presses the first contact perpendicularly to the pivot axis of the hub; moving the first jaw during a medical procedure, wherein moving the first jaw causes the first contact to slide on the circumferential edge; and applying a first electrical signal to the first jaw through the first contact.

21. The method of claim 20, further comprising: pressing a second contact against a constant-radius circumferential edge of a hub of a second jaw of the effector; moving the second jaw during the medical procedure, wherein moving the second jaw causes the second contact to slide on the circumferential edge of the hub of the second jaw; and applying a second electrical signal to the second jaw through the second contact.

22. The method of claim 21, wherein moving the first and second jaws comprises closing the jaws of the effector on a vessel, and applying the first and second signals heats and seals the vessel.

* * * * *